United States Patent
Woolfson et al.

(10) Patent No.: US 9,642,603 B2
(45) Date of Patent: May 9, 2017

(54) ARTICULABLE SURGICAL INSTRUMENT

(71) Applicant: MICROLINE SURGICAL, INC., Beverly, MA (US)

(72) Inventors: Steven B. Woolfson, Boston, MA (US); Sharad H Joshi, Hopkinton, MA (US); Jean-Luc Boulnois, Beverly, MA (US); Albert A. LePage, Beverly, MA (US); Christopher Devlin, Wakefield, MA (US)

(73) Assignee: MICROLINE SURGICAL, INC., Beverly, MA (US)

( * ) Notice: Subject to any disclaimer, the term of this patent is extended or adjusted under 35 U.S.C. 154(b) by 299 days.

(21) Appl. No.: 14/499,827

(22) Filed: Sep. 29, 2014

(65) Prior Publication Data

US 2015/0018843 A1 Jan. 15, 2015

Related U.S. Application Data

(62) Division of application No. 12/850,905, filed on Aug. 5, 2010, now Pat. No. 8,900,267.

(51) Int. Cl.
*A61B 17/00* (2006.01)
*A61B 17/02* (2006.01)
(Continued)

(52) U.S. Cl.
CPC .... *A61B 17/00234* (2013.01); *A61B 17/0218* (2013.01); *A61B 17/3478* (2013.01);
(Continued)

(58) Field of Classification Search
CPC .......... A61B 17/00234; A61B 17/0218; A61B 2090/0817; A61B 2090/701;
(Continued)

(56) References Cited

U.S. PATENT DOCUMENTS 5,454,827 A 10/1995 Aust et al.
5,599,151 A 2/1997 Daum et al.
(Continued)

FOREIGN PATENT DOCUMENTS

| EP | 2133028 A2 | 12/2009 |
|---|---|---|
| JP | 11-253389 A | 9/1999 |
| JP | 2006-061364 A | 3/2006 |

OTHER PUBLICATIONS

German Office Action, mailed Feb. 8, 2016, with respect to German Application No. 11 175 526.0, along with an English translation thereof.
(Continued)

*Primary Examiner* — Katrina Stransky
(74) *Attorney, Agent, or Firm* — Greenblum & Bernstein, P.L.C.

(57) ABSTRACT

An instrument includes, a lumen, a handpiece affixed to the proximal end of the lumen and including an actuator, a proximal articulable segment, the proximal end of the proximal articulable segment pivotably attached to the distal end of the lumen via a proximal hinge pin extending in a direction generally perpendicular to a longitudinal axis of the lumen, an actuation cable extending from the actuator through the lumen and into the proximal articulable segment, and a cable router comprising a proximal pulley assembly rotatable about the proximal hinge pin, wherein the cable is wrapped about the proximal pulley assembly.

20 Claims, 13 Drawing Sheets

(51) Int. Cl.
   *A61B 17/34* (2006.01)
   *A61B 17/29* (2006.01)
   *A61B 17/32* (2006.01)
   *A61B 90/70* (2016.01)
   *A61B 90/00* (2016.01)

(52) U.S. Cl.
   CPC ............. *A61B 2017/00323* (2013.01); *A61B 2017/291* (2013.01); *A61B 2017/2908* (2013.01); *A61B 2017/2927* (2013.01); *A61B 2017/2931* (2013.01); *A61B 2017/320044* (2013.01); *A61B 2090/0817* (2016.02); *A61B 2090/701* (2016.02)

(58) Field of Classification Search
   CPC ...... A61B 17/3478; A61B 2017/00323; A61B 2017/2908; A61B 2017/2927; A61B 2017/291; A61B 2017/320044; A61B 2017/2931
   See application file for complete search history.

(56) References Cited

U.S. PATENT DOCUMENTS

| | | |
|---|---|---|
| 5,643,311 A | 7/1997 | Smith et al. |
| 7,963,976 B2 | 6/2011 | Goldfarb et al. |
| 7,976,559 B2 | 7/2011 | Goldfarb et al. |
| 8,900,267 B2 * | 12/2014 | Woolfson ............ A61B 17/0218 600/141 |
| 2002/0103476 A1 | 8/2002 | Madhani et al. |
| 2005/0222601 A1 | 10/2005 | Erhard |
| 2005/0273084 A1 | 12/2005 | Hinman et al. |
| 2006/0094932 A1 | 5/2006 | Goldfarb et al. |
| 2006/0199999 A1 * | 9/2006 | Ikeda ................... A61B 1/0052 600/141 |
| 2007/0233052 A1 | 10/2007 | Brock |
| 2008/0046122 A1 | 2/2008 | Manzo et al. |
| 2009/0312773 A1 | 12/2009 | Cabrera et al. |
| 2010/0004663 A1 | 1/2010 | Murphy et al. |
| 2010/0016852 A1 | 1/2010 | Manzo et al. |
| 2010/0106167 A1 | 4/2010 | Boulnois et al. |

OTHER PUBLICATIONS

Japan Office action, dated Dec. 16, 2014 along with an English translation thereof.
E.P.O. Office action for Application No. 11 175 527 8, mail date is Oct. 22, 2014.
Japan Office Action, dated Jun. 3, 2014 along with an English translation thereof.
Japan Office action, mail date is Mar. 26, 2013.
E.P.O. Office action for Application No. 11 175 526 0, mail date is Oct. 22, 2014.
Office Action issued in Japan family member Patent Appl. No. 2013-123516, dated Aug. 18, 2015, along with an English translation thereof.

* cited by examiner

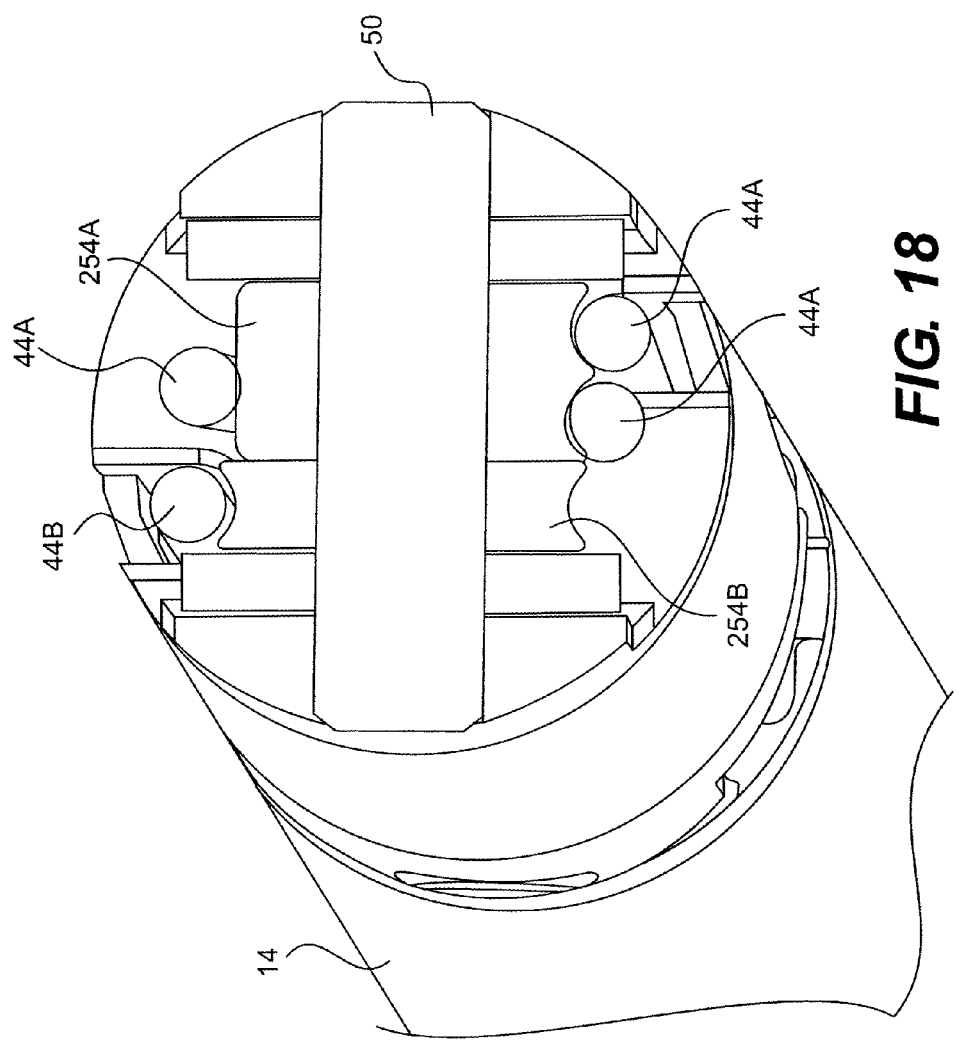

ARTICULABLE SURGICAL INSTRUMENT

CROSS-REFERENCE TO RELATED APPLICATION

This application is a divisional of pending U.S. application Ser. No. 12/850,905, filed Aug. 5, 2010, the disclosure of which is expressly incorporated herein by reference in its entirety.

BACKGROUND

1. Field of the Disclosure

The present disclosure relates to the field of laparoscopic surgical instruments. More particularly, the present disclosure relates to laparoscopic surgical instruments having an articulatable tool end.

2. Background Information

There has been a trend to perform surgery in the most minimally-invasive way. To this end, laparoscopic surgical instruments generally include a tube having an articulable distal end for performing a medical or surgical procedure to be performed, have been widely used because the incision necessary for insertion of such a tool on a medical device is typically small in comparison to alternative methods. As a result of the relatively smaller incision in comparison to open surgery, patients typically exhibit more rapid healing times and often experience fewer complications as a result of surgeries using such medical devices. Related art articulable surgical instruments are designed to mimic a surgeon's natural hand and/or finger motion in order to provide the surgeon with a safer, more natural-feeling mechanism by providing more natural feedback to the surgeon.

Such related art surgical instruments tend to have insertion portions (e.g., the lumen, stem or tube) having an outer diameter of 10 millimeters (mm) or greater, due to the amount of complicated mechanisms inside the instrument. While such articulated surgical instruments are laparoscopic in nature due the small incision in comparison to open surgery, there is a trend to make such laparoscopic incisions even smaller and in a lesser amount, thereby even further reducing the risk of complications from surgery, for example, by providing insertion portions having an outer diameter of 5 mm or less. When providing such a small surgical instrument, the internal components must be correspondingly reduced in number and size, but still must be robust enough to reliably perform the surgical procedure.

FIG. 9 shows schematic cross-sectional view of a related art surgical instrument 910. The instrument has a hollow lumen 912 affixed to an end segment 914 pivotably connected too the lumen by a joint 918, also referred to as a knuckle. Threaded within the lumen 912 and end segment 914 is an actuation cable 922. One end of the actuation cable 922 is affixed to a distal portion of the end segment 914, and another end of the actuation cable is affixed to a trigger (not shown). Actuation of the trigger creates tension in the articulation cable 922, the force of which pivots the end segment 914 at the knuckle 918 relative to the lumen 912. When the end segment 914 and lumen 912 are bent to a 90 degree angle (as shown), the cable 922 exits the confines of the instrument 910, subjecting it to damage and possible failure, thereby risking injury to the patient. Further, when the end segment 914 and lumen 912 are bent to such a 90 degree angle, the cable 922 drags over sharp edges 914E, 912E respectively formed at the ends of the end segment 914 and lumen 912, thereby subjecting the cable to fraying and possible failure, thereby risking injury to the patient.

Other related art surgical instruments propose using polymers at the knuckle region; however, such polymers have a very limited service life. Still other related art robotic surgical instruments use a micro sheave with a ball or roller bearing; however, such a configuration is costly and, due the precise nature of the bearings and high load on the cables, such instruments are reusable only a limited number of times (e.g., ten times).

In view of the above, a need has arisen for an articulable surgical instrument having a small outer diameter, yet having a reliable and safe articulation mechanism.

SUMMARY OF THE DISCLOSURE

According to a non-limiting feature of the disclosure, provided is a uni-directional articulating 5 mm surgical instrument which allows the user to navigate the working tip around internal anatomical structures, vessels and organs with motions and forces that mimic those of the Surgeon's finger during minimally invasive procedures. A non-limiting feature of the device allows for articulating retraction and blunt dissection utilizing a variety instrument tips, which may be disposable (single use) or reusable.

According to a non-limiting aspect of the disclosure, an instrument is provided which includes, a lumen having a proximal end and a distal end, a handpiece affixed to the proximal end of the lumen and including an actuator, proximal articulable segment having a proximal end and a distal end, the proximal end of the proximal articulable segment pivotably attached to the distal end of the lumen via a proximal hinge pin extending in a direction generally perpendicular to a longitudinal axis of the lumen, an actuation cable extending from the actuator through the lumen and into the proximal articulable segment, and, a cable router having a proximal knuckle assembly having a proximal segment knuckle affixed to an inner wall of the proximal end of the proximal articulable segment, a lumen knuckle affixed to an inner wall of the distal end of the lumen, and a proximal hinge pin knuckle positioned about the proximal hinge pin at a position between the proximal segment knuckle and the lumen knuckle, wherein the cable is bent against the proximal segment knuckle, the lumen knuckle and the proximal hinge pin knuckle when the proximal articulable segment is generally parallel with the lumen.

In the disclosure, the proximal segment knuckle, the lumen knuckle and the proximal hinge pin knuckle may be collectively configured to route the actuation cable through the lumen and the proximal articulable segment such that the actuation cable remains within the confines of the lumen and proximal articulable segment at an angle created when the proximal articulable segment is moved relative to the lumen.

Also in the disclosure, the actuation cable may be stainless steel wire strands. The proximal articulable segment may be limited in travel about the proximal hinge pin to a range of 0 and 90 degrees of the longitudinal axis of the lumen.

Also provided may be a distal articulable segment having a proximal end and a distal end, the proximal end of the distal articulable segment pivotably attached to the distal end of the proximal articulable segment via a distal hinge pin extending in a direction generally perpendicular to a longitudinal axis of the lumen, wherein the cable router further has a distal knuckle assembly having, a distal articulable segment knuckle affixed to an inner wall of the proximal end of the distal articulable segment, a distal segment knuckle affixed to an inner wall of the distal end of the proximal articulable segment, and a distal hinge pin knuckle positioned about the distal hinge pin at a position between the distal articulable segment knuckle and the distal segment knuckle, wherein the cable is bent about the distal articulable segment knuckle, the distal segment knuckle and the distal hinge pin knuckle when the proximal and distal articulable segments are generally parallel with the lumen.

The proximal articulable segment may be limited in travel about the proximal hinge pin to a range of approximately 0 and approximately 90 degrees of the longitudinal axis of the lumen, and the distal articulable segment may be limited in travel about the distal hinge pin to a range of approximately 0 and approximately 90 degrees of a longitudinal axis of the proximal articulable segment such that the distal articulable segment is limited in travel to a range of approximately 0 and approximately 180 degrees of the longitudinal axis of the lumen.

Additionally, the handpiece may have an articulation lock configured to removably lock the finger actuator such that the proximal articulable segment is correspondingly locked from pivoting.

The handpiece may have a nosepiece and a handle and a handle rotation release located on one of the nosepiece and handle and configured to removably lockably provide for the rotatable positioning of the handle relative to the nosepiece.

Further, the lumen and the proximal articulable segment may have an outer diameter of approximately 5 millimeters, and the actuation cable has a diameter of approximately 0.027 of an inch.

Also, the actuation cable may be bent about the proximal segment knuckle, the lumen knuckle and the proximal hinge pin knuckle at a portion of the actuation cable configured to pivot the proximal articulable element relative to the lumen, and the actuation cable may be generally parallel with the proximal articulable segment and the lumen at a portion of the actuation cable configured to return the proximal articulable segment generally parallel with the lumen.

The actuation cable may have first and second actuation cables, wherein the first actuation cable is bent about the proximal segment knuckle, the lumen knuckle and the proximal hinge pin knuckle at a portion of the actuation cable configured to pivot the proximal articulable element relative to the lumen, and the second actuation cable is generally parallel with the proximal articulable segment and the lumen at a portion of the actuation cable configured to return the proximal articulable segment generally parallel with the lumen.

Also, the outer diameter of the lumen may be approximately 5 millimeters and the outer diameter of the actuation cable is 0.027 inches. Further, the proximal hinge pin knuckle may have an eccentric outer circumference.

During initial tensioning of the actuation cable, the segment knuckle and the lumen knuckle may cause the actuation cable to exert a force against the proximal hinge pin knuckle in a direction generally orthogonal to the longitudinal axis of the lumen.

During tensioning of the actuation cable subsequent to the initial tensioning, the actuation cable may disengage from the proximal hinge pin knuckle and exert a force in a direction different from the force against the proximal hinge pin knuckle, such that the actuation cable moves the proximal articulable segment relative to the lumen.

According to another non-limiting aspect of the disclosure an instrument may include a lumen having a proximal end and a distal end, a handpiece affixed to the proximal end of the lumen and including an actuator, proximal articulable segment having a proximal end and a distal end, the proximal end of the proximal articulable segment pivotably attached to the distal end of the lumen via a proximal hinge pin extending in a direction generally perpendicular to a longitudinal axis of the lumen, an actuation cable extending from the actuator through the lumen and into the proximal articulable segment, and a cable router having a proximal pulley assembly rotatable about the proximal hinge pin, wherein the cable is wrapped about the proximal pulley assembly.

Also, the cable may be wrapped approximately 360 degrees about the proximal pulley assembly.

During tensioning of the actuation cable to pivot the proximal articulable segment to a position oblique to the lumen, the cable may translate about the proximal pulley assembly and cause the proximal pulley assembly to rotate.

Further, an outer circumference of the proximal pulley assembly may have a helical channel through which the cable is wrapped.

Also provided may be a distal articulable segment having a proximal end and a distal end, the proximal end of the distal articulable segment pivotably attached to the distal end of the proximal articulable segment via a distal hinge pin extending in a direction generally perpendicular to a longitudinal axis of the lumen, wherein the cable router further has a distal knuckle assembly having a distal pulley assembly rotatable about the distal hinge pin, wherein the cable is wrapped about the distal pulley assembly. The cable may be wrapped approximately 360 degrees about the distal pulley assembly.

Additionally, an outer circumference of the distal pulley assembly may have a helical channel through which the cable is wrapped.

Also provided may be an adjuster affixed to a distal end of the actuation cable at the distal articulable segment, wherein the actuation cable is a single cable extending from the actuator through the lumen, the proximal articulable segment, the distal articulable segment, and back to the actuator, the actuation cable having an actuating section bent about the proximal segment knuckle, the lumen knuckle and the proximal pulley assembly and configured to pivot the proximal articulable element relative to the lumen, and a returning section generally parallel with the proximal articulable segment and the lumen and configured to return the proximal articulable segment generally parallel with the lumen, and the adjuster is configured to prevent translation of the actuation cable about the distal end of the distal articulable segment.

The adjuster may further have a locking bar extending in a direction generally parallel with the distal hinge pin and about which the distal end of the actuation cable bends at the distal articulable segment, a cam bar positioned at the distal articulable element and configured to removably adjustably prevent translation of the actuation cable by removably adjustably impinging the actuation cable against the locking bar. Also, an outer circumference of the locking bar may have a helical channel through which the cable is bent.

Further, in a radial direction, an angle created by the actuating section of the actuation cable and the returning section of the actuation cable with a longitudinal axis of the lumen may be oblique.

A distalmost end of the distal articulable segment may be configured to removably accommodate a surgical tool therein.

Additionally, the proximal pulley assembly may have first and second proximal pulleys coaxially rotatable about the proximal hinge pin, and the actuation cable may have an actuating section wrapped about the first proximal pulley, and a returning section wrapped about the second proximal pulley. During actuation of the actuation cable, the actuating section may translate over and causes the first proximal pulley to rotate about the proximal hinge pin, and the returning section translates over and causes the second proximal pulley to rotate about the proximal hinge pin in a direction opposite the rotation direction of the first proximal pulley.

Also, the proximal pulley assembly may have first and second proximal pulleys coaxially rotatable about the proximal hinge pin, and the distal pulley assembly may have first and second distal pulleys coaxially rotatable about the distal hinge pin. The actuation cable may have an actuating section wrapped about the first proximal pulley and first distal pulley, and a returning section wrapped about the second proximal pulley and second distal pulley. During actuation of the actuation cable, the actuating section may translate over and causes the first proximal and distal pulleys to respectively rotate about the proximal and distal hinge pins, and the returning section may translate over and causes the second proximal and distal pulleys to respectively rotate about the proximal and distal hinge pins in a direction opposite the rotation direction of the first proximal and distal pulleys.

Also provided may be a method of operating an instrument, the instrument having a lumen having a proximal end and a distal end, an actuator affixed to the proximal end of the lumen, proximal articulable segment having a proximal end and a distal end, the proximal end of the proximal articulable segment pivotably attached to the distal end of the lumen via a proximal hinge pin extending in a direction generally perpendicular to a longitudinal axis of the lumen, an actuation cable extending from the actuator through the lumen and into the proximal articulable segment, and a cable router having a proximal knuckle assembly having a proximal segment knuckle affixed to an inner wall of the proximal end of the proximal articulable segment, a lumen knuckle affixed to an inner wall of the distal end of the lumen, and a proximal hinge pin knuckle affixed about the proximal hinge pin at a position between the proximal segment knuckle and the lumen knuckle, wherein the cable is bent against the proximal segment knuckle, the lumen knuckle and the proximal hinge pin knuckle when the proximal articulable segment is generally parallel with the lumen, and the method including initially actuating the actuator to provide tension the actuation cable over the proximal segment knuckle and lumen knuckle such that the actuation cable exerts a force against the proximal hinge pin knuckle in a direction generally orthogonal to the longitudinal axis of the lumen, subsequently actuating the actuator, subsequent to said initially actuating, such that the actuation cable exerts a force in a direction different from the force against the proximal hinge pin knuckle and translates the actuation cable over the proximal segment knuckle and lumen knuckle, and articulating the proximal articulable segment relative to the lumen.

Other exemplary embodiments and advantages of the present invention may be ascertained by reviewing the present disclosure and the accompanying drawings, and the above description should not be considered to limit the scope of the present invention.

BRIEF DESCRIPTION OF THE DRAWINGS

The present invention is further described in the detailed description which follows, in reference to the noted plurality of drawings, by way of non-limiting examples of preferred embodiments of the present invention, in which like characters represent like elements throughout the several views of the drawings, and wherein:

FIG. 18 shows a transverse cross-sectional schematic perspective view of the surgical instrument in an unarticulated position, according the second aspect of the present disclosure.

DETAILED DESCRIPTION

In view of the foregoing, the present disclosure, through one or more of its various aspects, embodiments and/or specific features or sub-components, is thus intended to bring out one or more of the advantages as specifically noted below.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
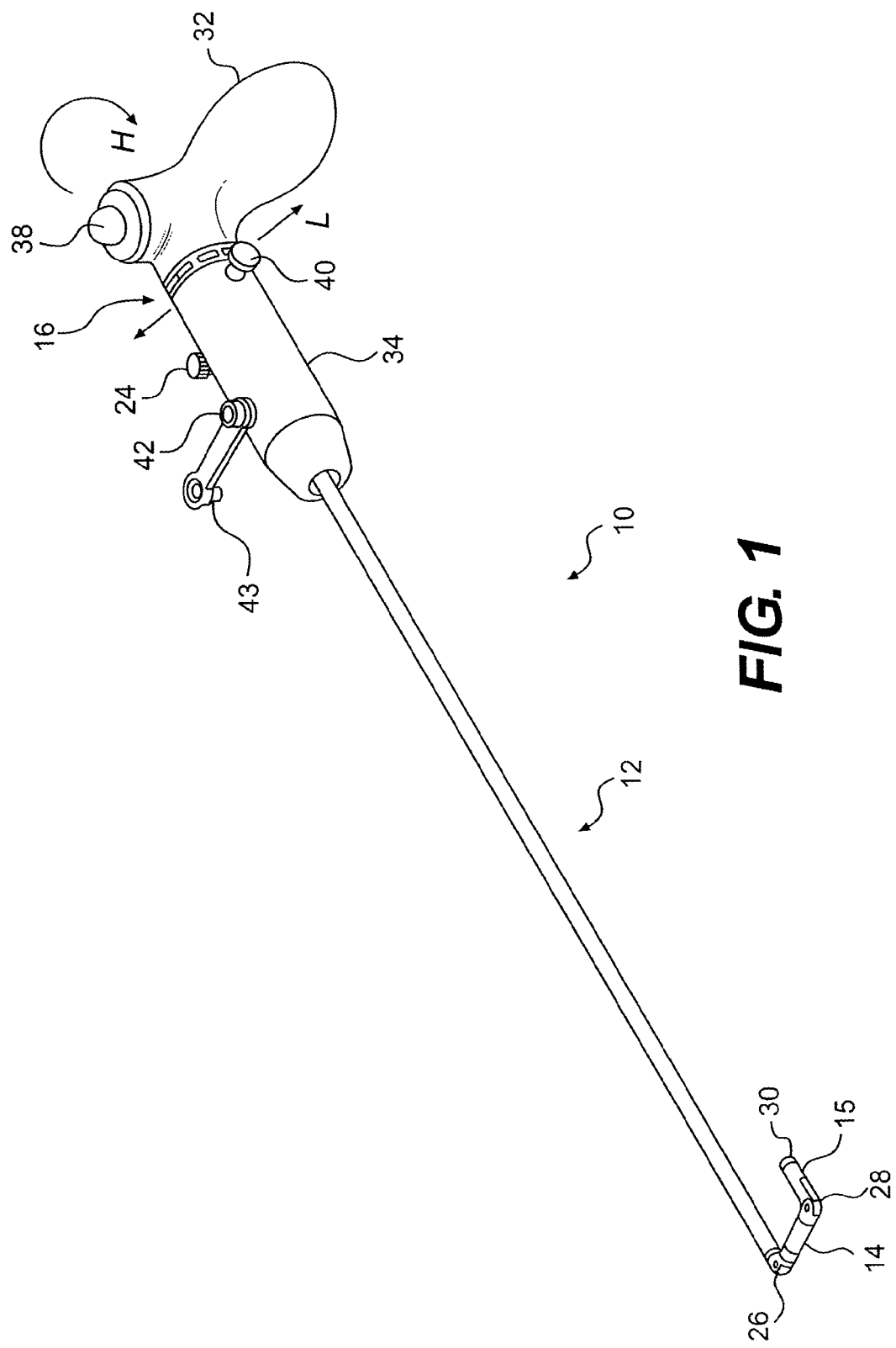
FIG. 1 shows a perspective view of the surgical instrument in an articulated position, according an aspect of the present disclosure.
Figure 2:
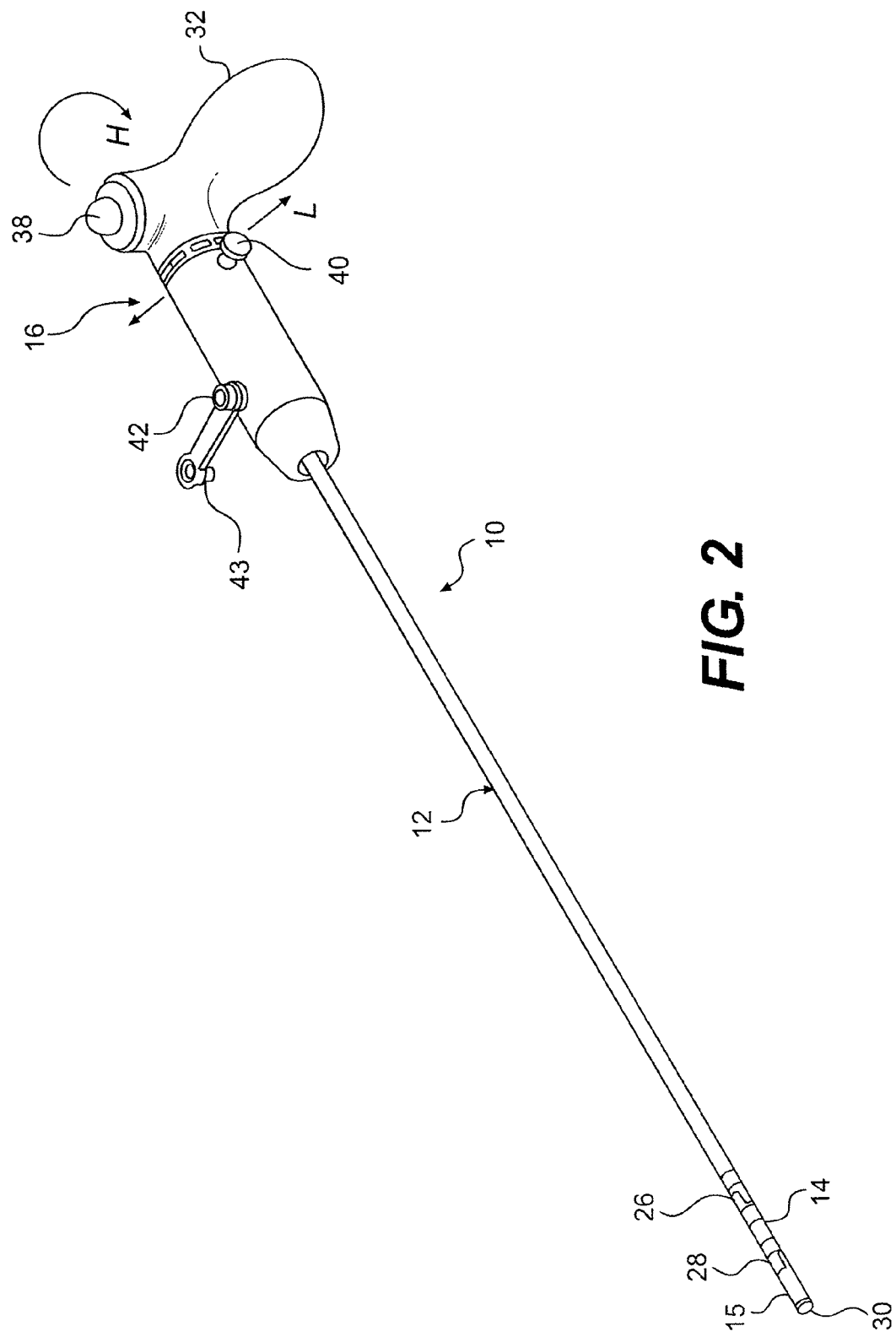
FIG. 2 shows a perspective view of the surgical instrument in an unarticulated position, according an aspect of the present disclosure.
Figure 3:
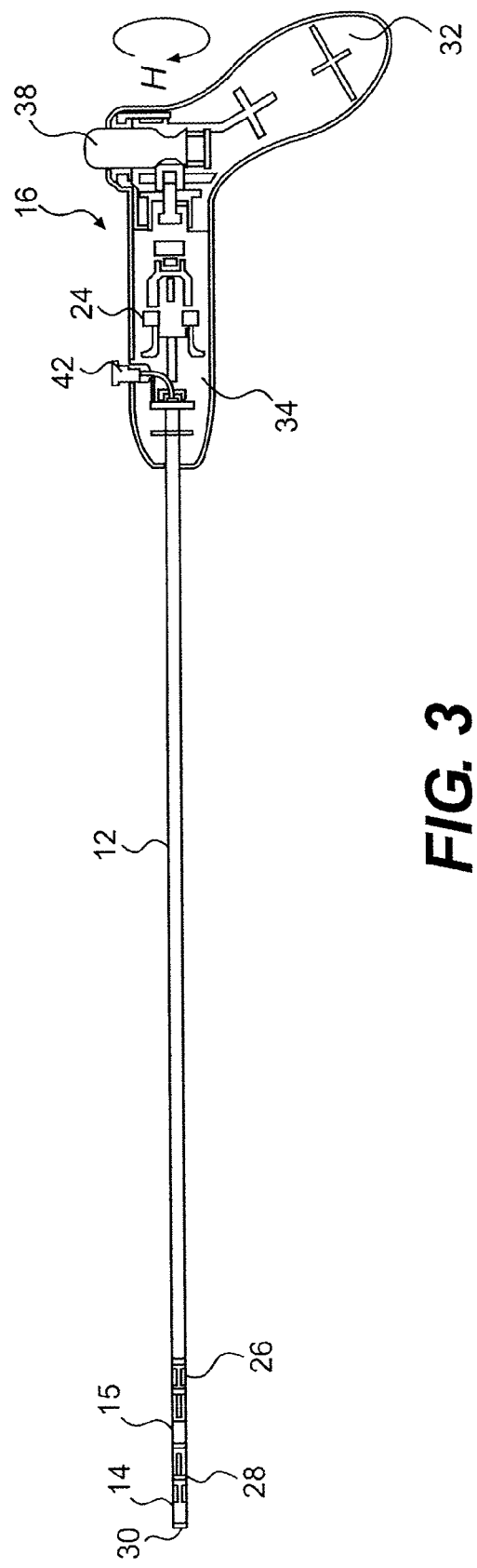
FIG. 3 shows a side sectional view of the surgical instrument in an unarticulated position, according an aspect of the present disclosure.

Referring now to the drawings wherein like characters represent like elements, FIGS. 1-3 show a surgical instrument 10 according to an aspect of the present disclosure. The instrument includes a lumen 12 having a proximal end affixed to a handpiece 16 at the distal end of the instrument 10. A proximal articulable segment 14 and a distal articulable segment 15 (also referred to as links) are provided at the distal end of the lumen. Specifically, a proximal end of the distal link 15 is a pivotably attached to a distal end of the proximal link 14 at a distal knuckle 28, and a proximal end of the proximal link is pivotably attached to the distal end of the lumen 12 at a proximal knuckle 26. The lumen 12, proximal link 14 and distal link 15 are collectively referred to as an insertion portion of the instrument. The insertion portion of the instrument 10 preferably has an outer diameter of 5 mm, although those of skill in the art will appreciate that in alternative embodiments the insertion portion can have an outer diameter of greater or less than 5 mm.

Each link is preferably pivotable from approximately 0 to approximately 90 degrees such that when the instrument 10 is fully actuated, the proximal link 14 forms approximately a 90 degree angle with the lumen 12, and the distal link 15 forms approximately a 90 degree angle with the proximal link 14 and approximately a 180 degree angle with the lumen, thereby approximating the range of motion of a human finger. Thus, the links 14, 15 are pivotable within a plane on only one side of the device. Although two links are shown, it is readily appreciable by those skilled in the art that one link or more than two links may be used in alternative embodiments.

According to a non-limiting feature of the present disclosure, the distal end of the distal link 15 may have a tip attachment section 30 to removably accommodate the attachment of a surgical tool, including but not limited to a kitner dissector, probe, syringe or any other suitable tool, which may be reusable or single-use (disposable).

The handpiece 16 has a trigger 24 that preferably operates within the same plane as the pivoting plane of the proximal and distal links 14, 15. The handpiece 16 includes a handle 32 affixed to a nosepiece 34. Also provided is a handle rotation release ball 38 which, when depressed, allows the handle 32 to rotate in (preferably) 90 degree increments about arrow H, and which, when released, locks the handle 32 in place. Rotation of the handle 32 by 180 degrees provides for left or right-handed operation, thereby increasing the versatility of the instrument 10. Also, the handle 32 is preferably a pistol-grip configuration for secure and comfortable manipulation, although the handle can have different suitable configurations in alternative embodiments.

The handpiece 16 may further include an articulation lock button 40 which serves to removably lock the links 14, 15 in different positions (nine positions, in the preferred embodiment) within their range of motion. To lock the instrument 10, the user pushes the lock button 40 in a direction along the arrow L, and to unlock the instrument, the user pushes the lock button 40 in an opposite direction along the arrow L. The handpiece 16 may also include a flushable luer 42 to facilitate cleaning after a surgical procedure, thereby enabling the instrument 10 to be reused. The luer 42 is covered by a removable luer cap 43 (shown removed from the luer in FIGS. 1-2), which covers the luer to prevent unwanted material from entering the instrument 10.

Figure 7:
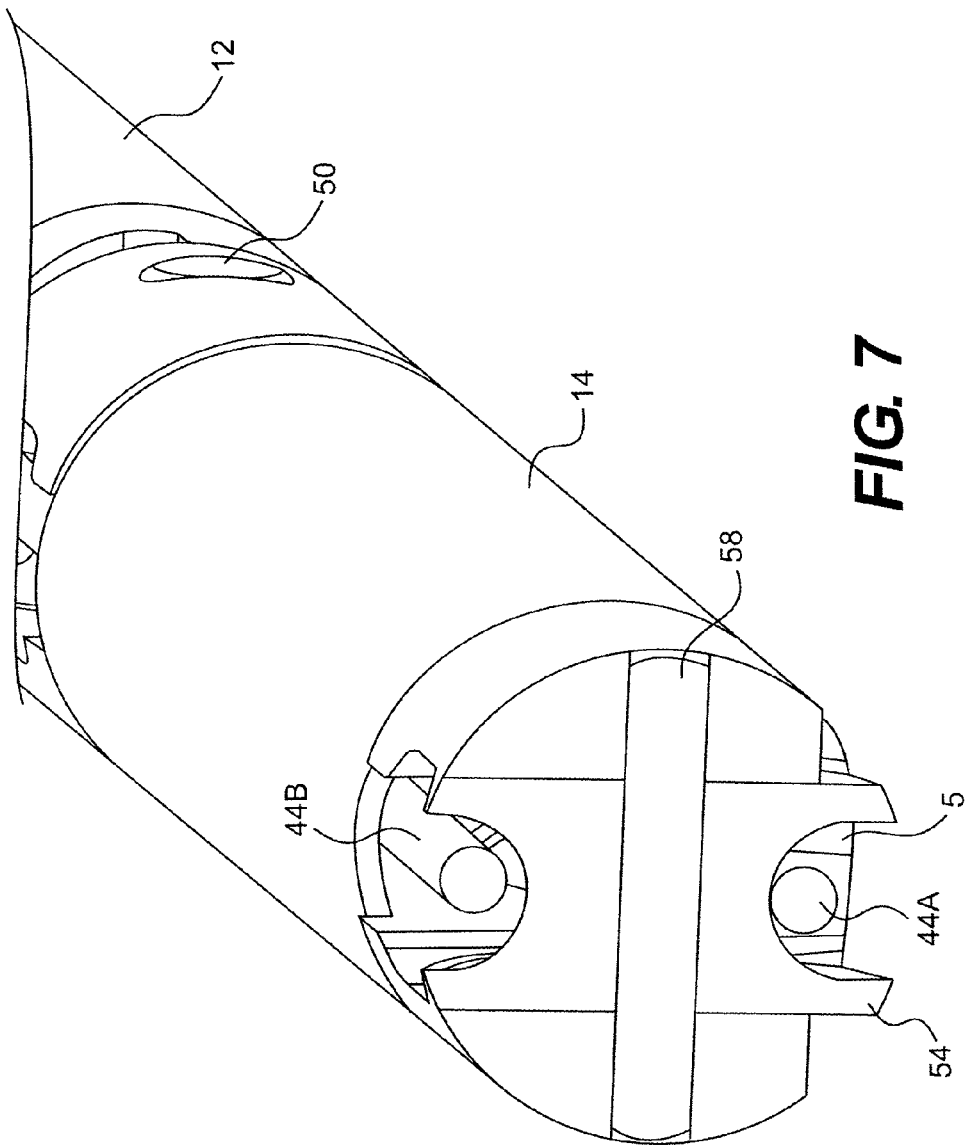
FIG. 7 shows a transverse cross-sectional schematic perspective view of the surgical instrument in an unarticulated position, according an aspect of the present disclosure.
Figure 8:
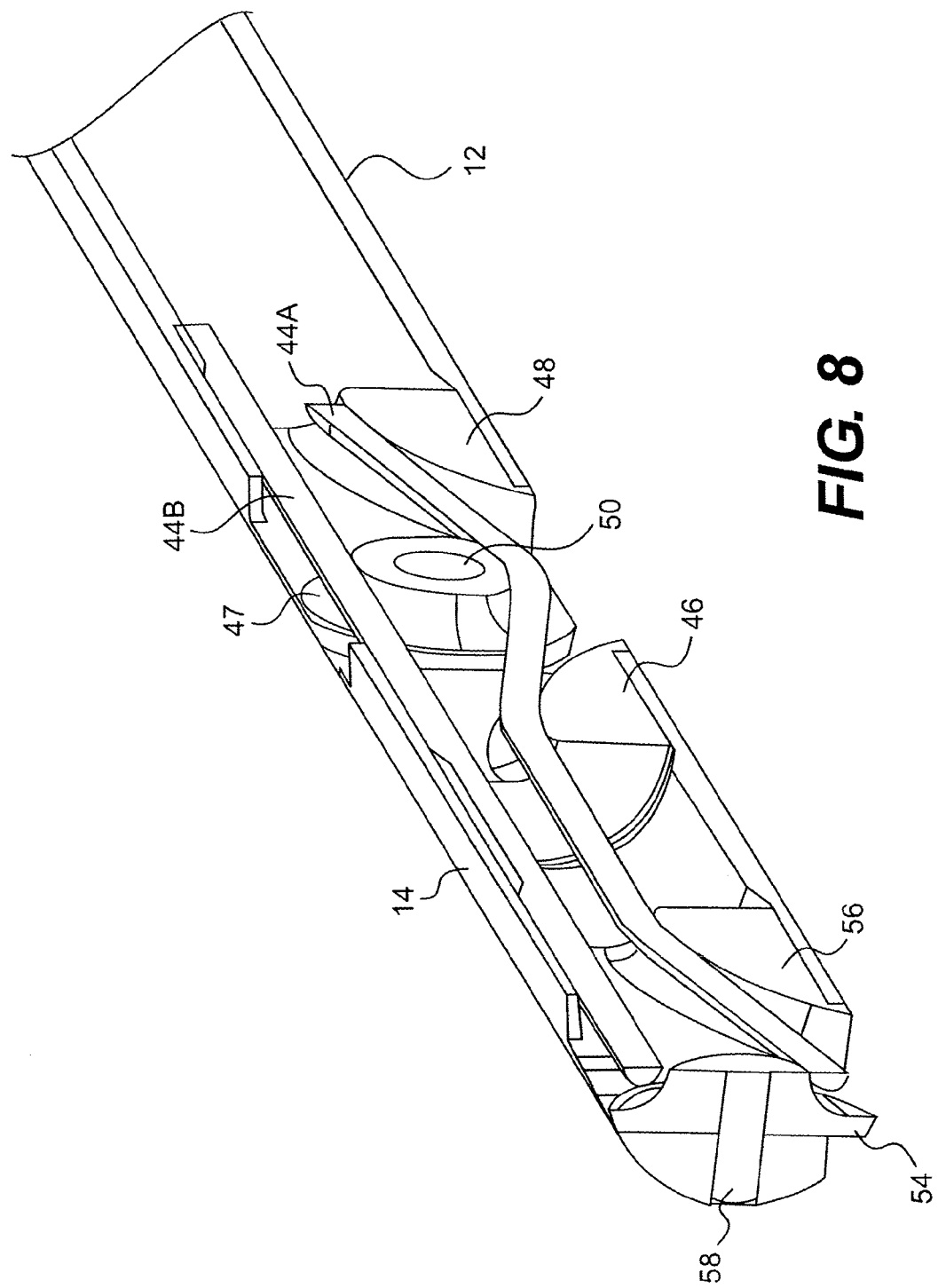
FIG. 8 shows a partial transverse cross-sectional, side schematic perspective view of the surgical instrument in an unarticulated position, according an aspect of the present disclosure.
Figure 9:
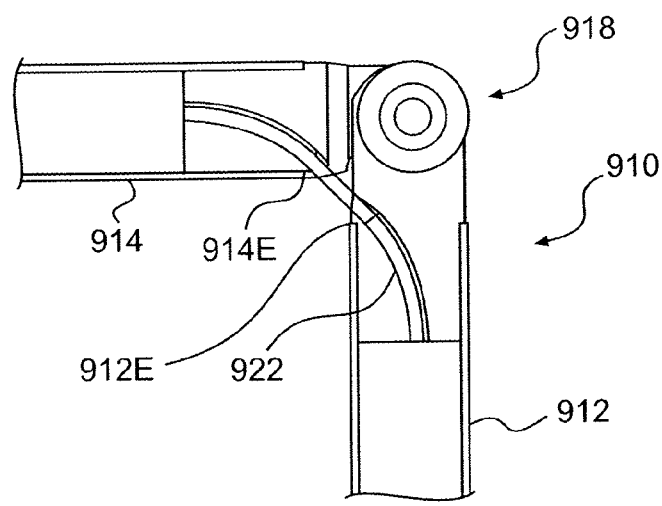
FIG. 9 shows a partial side-sectional view of a related art surgical instrument in an articulated position.

The instrument 10 includes an actuation cable 44A, 44B extending through the instrument. Specifically, the cable 44A, 44B is attached to the trigger 24 and extends though the lumen 12, proximal link 14 and distal link 15 along one side of the inside of insertion portion (i.e., the side where the proximal and distal links pivot to create an angle with the lumen 12) where it is affixed to the distal end of the distal link. The cable 44A, 44B then returns along another side of the inside of the insertion portion (i.e., the opposite side of the lumen 12 from where the proximal and distal links pivot to create an angle with the lumen 12) where it is again attached to the trigger, as shown in FIGS. 7-8.

The cable 44A, 44B may be a single cable continuously extending from the trigger 24, through the insertion portion and back to the trigger, or alternatively may be on one or more parts extending from the trigger, through the insertion portion and back to the trigger. The portion of the cable or cables extending on the side of the insertion portion where the proximal and distal links pivot to create an angle with the lumen 12 is referred to as the actuating section 44A, and the portion of the cable or cables extending opposite side of the lumen 12 from where the proximal and distal links pivot to create an angle with the lumen 12 is referred to as the returning section 44B.

The cable 44A, 44B is preferably made out of stainless steel wire strands and is 0.027 inches in diameter, although it is appreciable by those skilled in the art that any suitable material of varying configurations, and that other cable dimensions and sizes may be used in alternative embodiments. The inventors have found that a stainless steel wire of 0.027 inches provides an ideal strength-to-size relationship with an insertion portion having an outer diameter of 5 mm, without compromising reliability of the device.

The proximal knuckle 26 and distal knuckle 28 each include a knuckle assembly. Specifically and as shown in FIGS. 4-8 and 10-11, the proximal knuckle 26 includes a lumen knuckle 48 located on the inner wall of the lumen 12, a proximal hinge pin knuckle 47, and a proximal segment knuckle 46 located on the inner wall of the proximal link 14, located in this order from the lumen. The hinge pin knuckle 47 is positioned about a hinge pin 50 about which the proximal link 14 pivots. The lumen knuckle 48 and proximal segment knuckle 46 are preferably mirror images of each other, although such is not a requirement.

Also the distal knuckle 28 includes a distal articulated segment knuckle 52 located on the inner wall of the distal link 15, a distal hinge pin knuckle 54, and a distal segment knuckle 56 located on the inner wall of the distal end of the proximal link 14, located in this order from the distal link. The hinge pin knuckle 54 is positioned about a hinge pin 58 about which the proximal and distal links 14, 15 pivot. The distal articulated segment knuckle 52 and distal segment knuckle 56 are preferably mirror images of each other, although such is not a requirement. The hinge pin knuckles 47, 54 are described as separate components from the hinge pins 50, 58; however, in alternative embodiments they may be integrated such that the hinge pin knuckles 47, 54 have shafts penetrating into the walls of the insertion portion.

Figure 4:
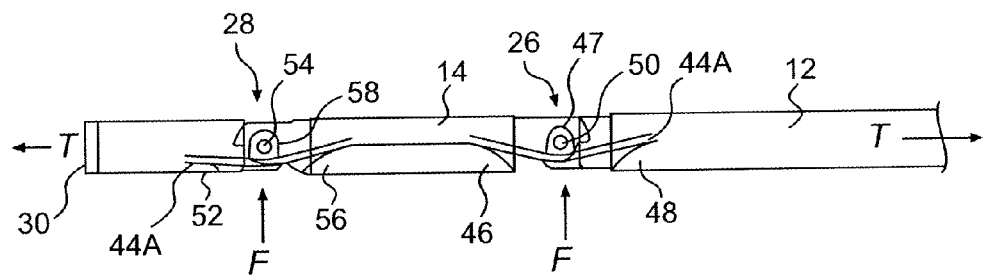
FIG. 4 shows a partial side sectional schematic view of the surgical instrument in an unarticulated position, according an aspect of the present disclosure.
Figure 10:
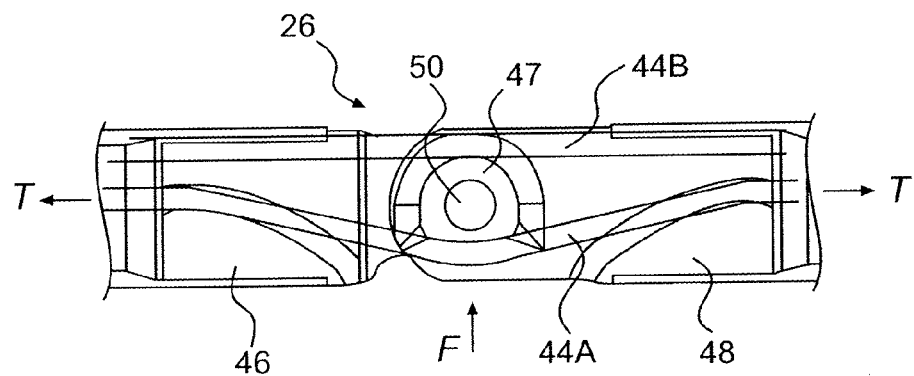
FIG. 10 shows a partial side sectional schematic view of the surgical instrument in an unarticulated position, according an aspect of the present disclosure.
Figure 11:
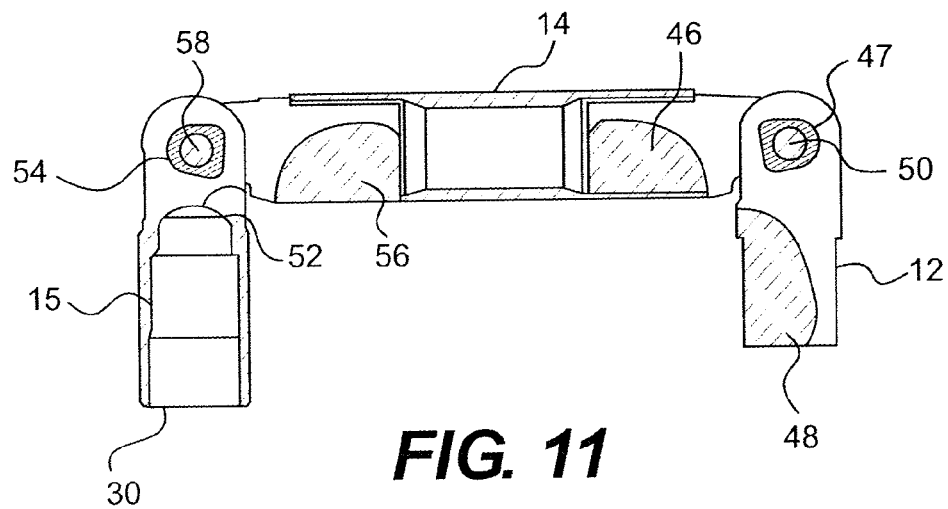
FIG. 11 shows a partial side sectional schematic view of the surgical instrument in an articulated position, according an aspect of the present disclosure.

As shown in FIGS. 8, 10 and 11, the lumen knuckle 48, proximal segment knuckle 46, distal articulated segment knuckle 52, and distal segment knuckle 56 (collectively referred to as the link knuckles) are preferably generally triangular in cross section along the longitudinal axis of the insertion portion. In other words, in cross section, the link knuckles 46, 48, 52 and 56 resemble right triangles having the hypotenuse in outwardly arcuate form. In alternative embodiments (as shown in FIG. 4), the proximal segment knuckle 46 and distal segment knuckle 56 may be a single piece as opposed to two distinct pieces.

The hinge pin knuckles 47, 54 each preferably have an eccentric (i.e., not a perfect circle) outer circumference and have a flared profile on their sides facing the actuating section 44A in order provide increased contact therewith (including circular). The link knuckles 46, 48, 52, 56 and hinge pin knuckles 47, 54 are collectively called a cable router.

The cable or cables 44A, 44B are routed as explained herein. As shown, e.g., in FIG. 6, from the trigger 24, the actuating section 44A passes along the inner side of the lumen 12. Once at the distal end of the lumen, the actuating section 44A bends over the lumen knuckle, under the hinge pin knuckle 47, over the proximal segment knuckle 46, under the distal hinge pin knuckle 54 and over the distal articulated segment knuckle 52, where the cable is affixed (i.e., translation of the cable is prevented) to the distal articulated segment 15. In embodiments where two cables is used, the preceding is the terminus of the actuating section 44A, and a new cable in the form of the returning section 44B is returned back to the trigger 24 on the opposite side of the device. In embodiments where a single cable 44A, 44B is used, after the actuating section 44A is affixed to the distal articulated segment 15 the returning section 44B is returned back to the trigger 24 on the opposite side of the device. Irrespective of whether single or plural cables 44A, 44B are used, the routing of the returning section 44B takes substantially the same shape of the proximal and distal links 14, 15 and the lumen 12 (i.e., the returning section 44B of the cable is not bend about any link knuckles 46, 48, 52, 56 in the preferred embodiment, but may be bent around knuckles in alternative embodiments). Also irrespective of whether single or plural cables 44A, 44B are used, it is preferable to prevent the cable from translating about the distalmost portion of cable travel, otherwise the cable will not articulate the links 14, 15, but will rather rotate in place like a conveyor belt.

Prior to using the instrument 10, a user first inserts an instrument tip (not shown) into the tip attachment section 30, via threading or other suitable methods of attachment. Alternatively, the tip may be integral or unitarily formed with the distal link 15. Once the instrument tip is fully secure, the user should ensure that the articulation lock 40 is released and that the links 14, 15 are straight. The user should also ensure that the luer 43 cap is securely installed over the flush port luer 42, and that the handle 32 is rotated to the desired position and ensure that it is securely locked in position.

The articulation of the instrument 10 is now described herein. At rest, and as shown in FIG. 4, a spring (not shown) in the nose piece 34 distally biases the trigger 24 so that the links 14, 15 are straight (i.e., they are generally parallel with the lumen 12) to facilitate the insertion of the insertion portion into a body cavity of the patient. The user uses a finger to proximally pull the trigger 24, which in turn tenses the actuating section 44A in direction T such that the actuating section translates over link knuckles 46, 48, 52, 56 and hinge pin knuckles 47, 54, and the returning section 44B is correspondingly loosened. During this initial tension in direction T and as shown in FIGS. 4 and 10, the height of lumen knuckle 48 and proximal segment knuckle 46 with respect to the hinge pin knuckle 47 allows the segment knuckle and the lumen knuckle to cause the actuation cable to exert a force (upwards in FIG. 10 in direction of arrow F) against the proximal hinge pin knuckle to provide leverage to the actuation cable, thereby providing added strength to the instrument 10. In other words, the lumen knuckle 48 and proximal segment knuckle 46 offset the cable with respect to the hinge pin 50. The distal articulated segment knuckle 52 and distal segment knuckle 56 are similarly arranged to exert a similar force against the hinge pin knuckle 54.

Figure 5:
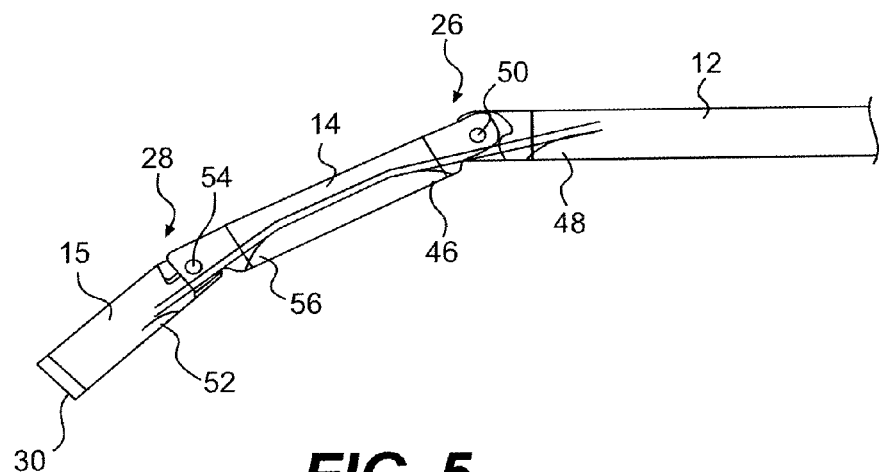
FIG. 5 shows a partial side sectional schematic view of the surgical instrument in a partially articulated position, according an aspect of the present disclosure.
Figure 6:
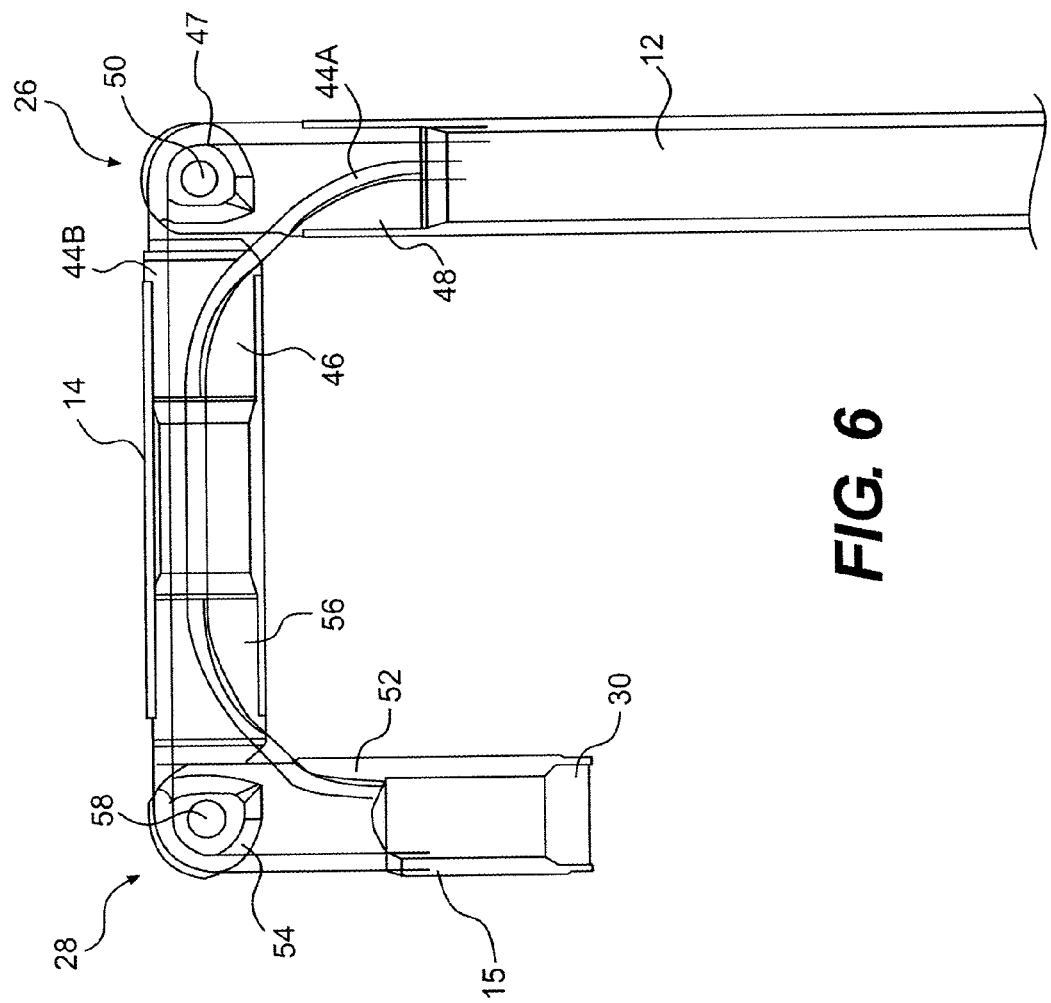
FIG. 6 shows a partial side sectional schematic view of the surgical instrument in an articulated position, according an aspect of the present disclosure.

As the trigger continues to be pulled proximally, the links 14, 15 begin to articulate, causing the hinge pin knuckles 47, 54 to disengage from the actuating section, and the cable 44A, 44B transitions from exerting force F on the hinge pin knuckles 47, 54 to exerting pulling force in a direction to articulate the links 14, 15, governed by the link knuckles 46, 48, 52, 56 (referred to as the "cam over" position), as shown in FIG. 5. As the trigger continues to be pulled proximally, increasing tension on the actuating section 44A causes the links 14, 15 to continue to articulate until the trigger reaches is proximalmost position and the links are fully articulated, as shown in FIGS. 1, 6 and 11. In the fully articulated position, the proximal link 14 creates a 90 degree angle with the lumen 12, and the distal link 15 creates a 90 degree angle with the proximal link 14 and creates a 180 degree angle with the lumen. Thus, the instrument 10 is able to exert forces in two different directions at two different stages of operation, namely, a stage exerting a force F against the hinge pin knuckles 47, 54, to a stage exerting pulling force in a direction to articulate the links 14, 15.

An additional benefit of the arrangement of the lumen knuckle 48 and proximal segment knuckle 46 with respect to the hinge pin knuckle 47, and of the arrangement of the distal articulated segment knuckle 52 and distal segment knuckle 56 with respect to the hinge pin knuckle 54 is that when the instrument is fully articulated, the cable (particularly the actuating section 44A) remains within the confines of the insertion portion, thereby reducing the risk of damage to the cable.

Figure 12:
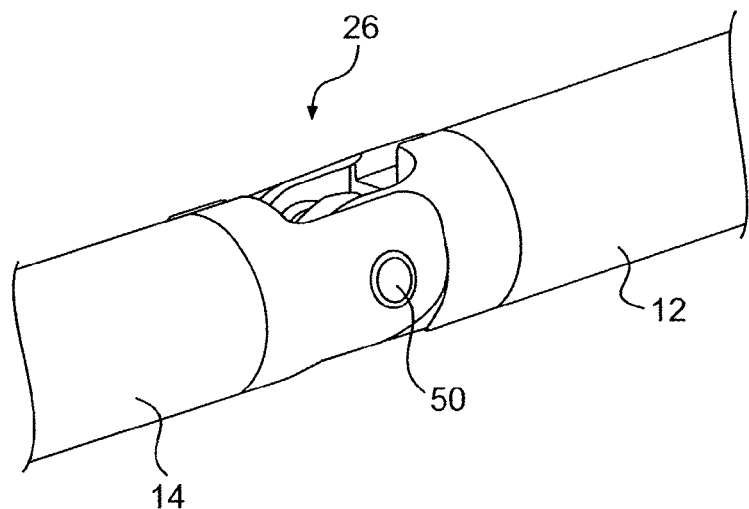
FIG. 12 shows a partial perspective schematic view of the surgical instrument in an unarticulated position, according to a second aspect of the present disclosure.
Figure 13:
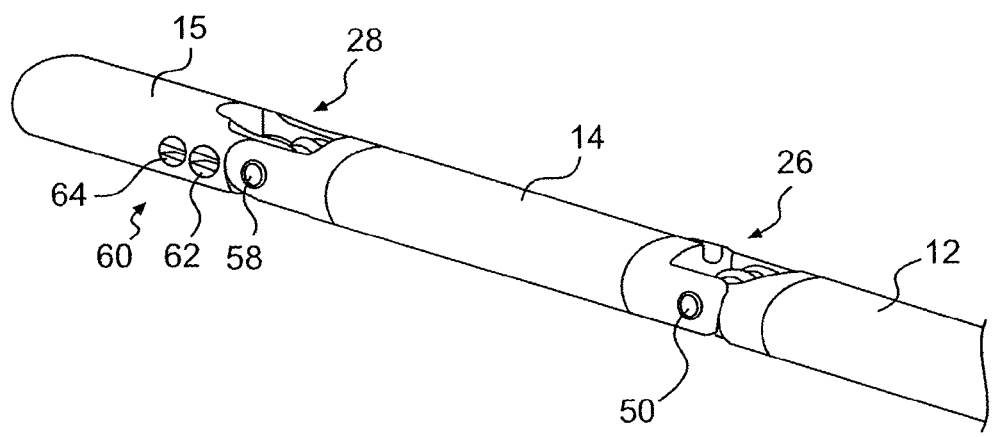
FIG. 13 shows an additional partial perspective schematic view of the surgical instrument in an unarticulated position, according to the second aspect of the present disclosure.
Figure 14:
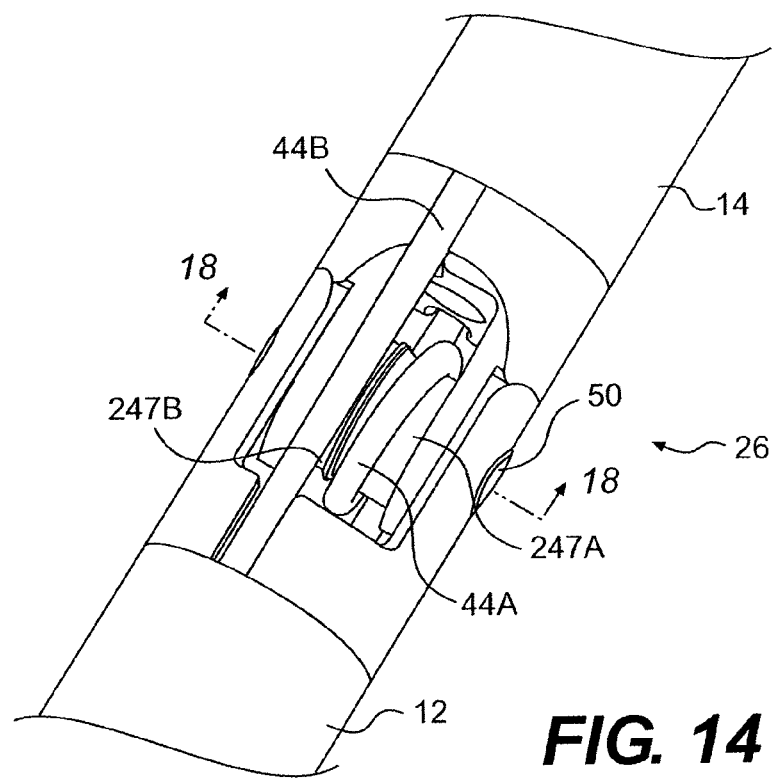
FIG. 14 shows a further partial perspective schematic view of the surgical instrument in an unarticulated position, according to the second aspect of the present disclosure.
Figure 15:
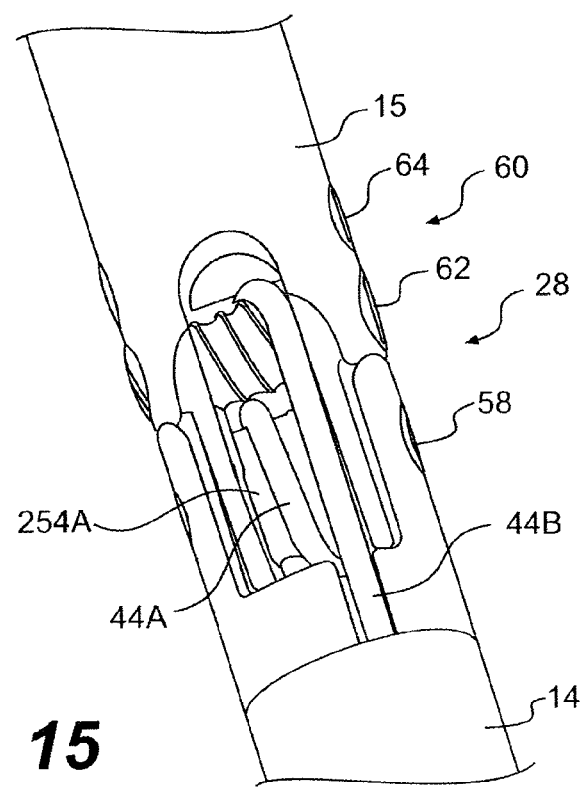
FIG. 15 shows another partial perspective schematic view of the surgical instrument in an unarticulated position, according to the second aspect of the present disclosure.
Figure 16:
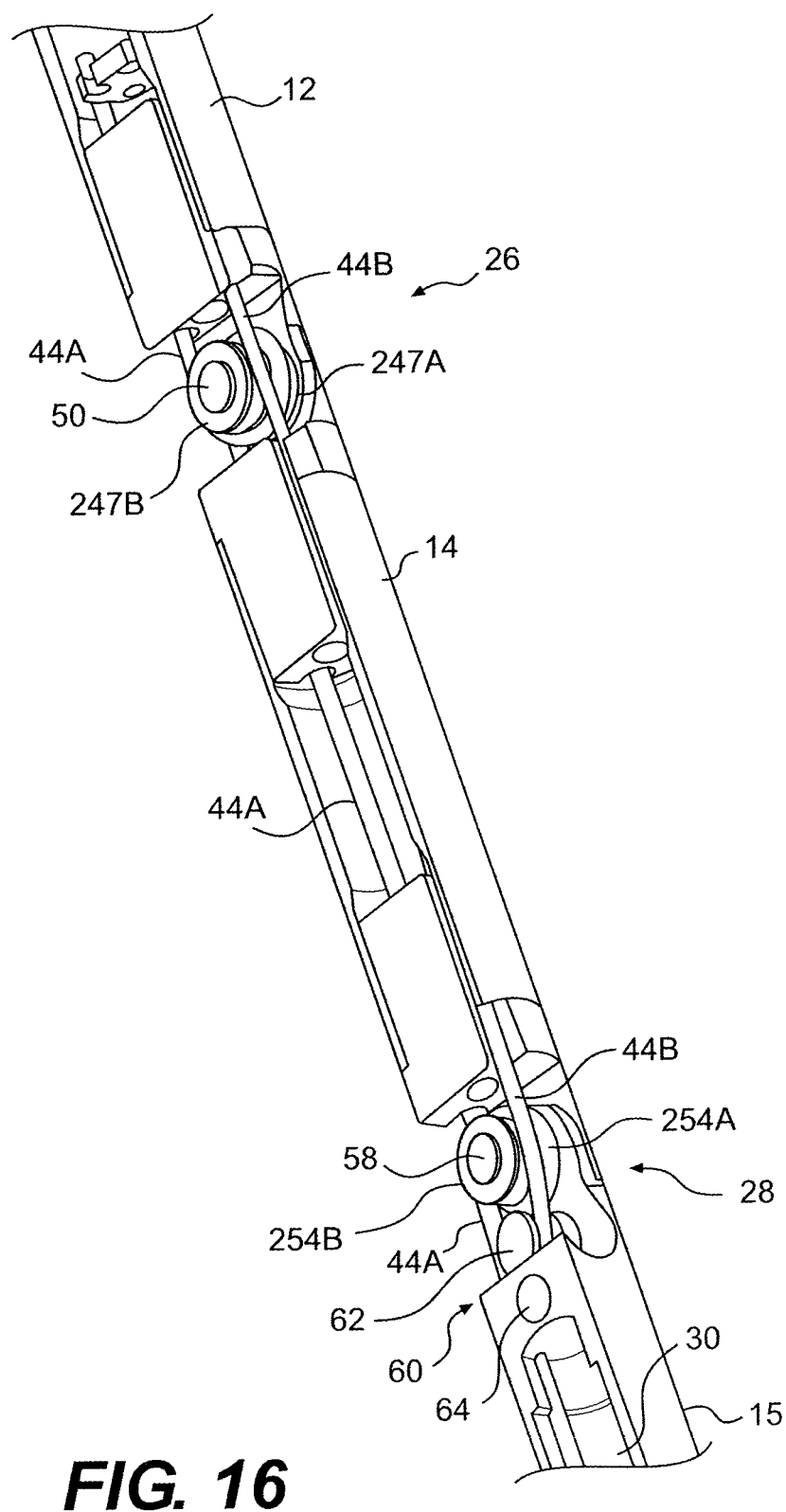
FIG. 16 shows another partial side-sectional schematic view of the surgical instrument in an unarticulated position, according to the second aspect of the present disclosure.
Figure 17:
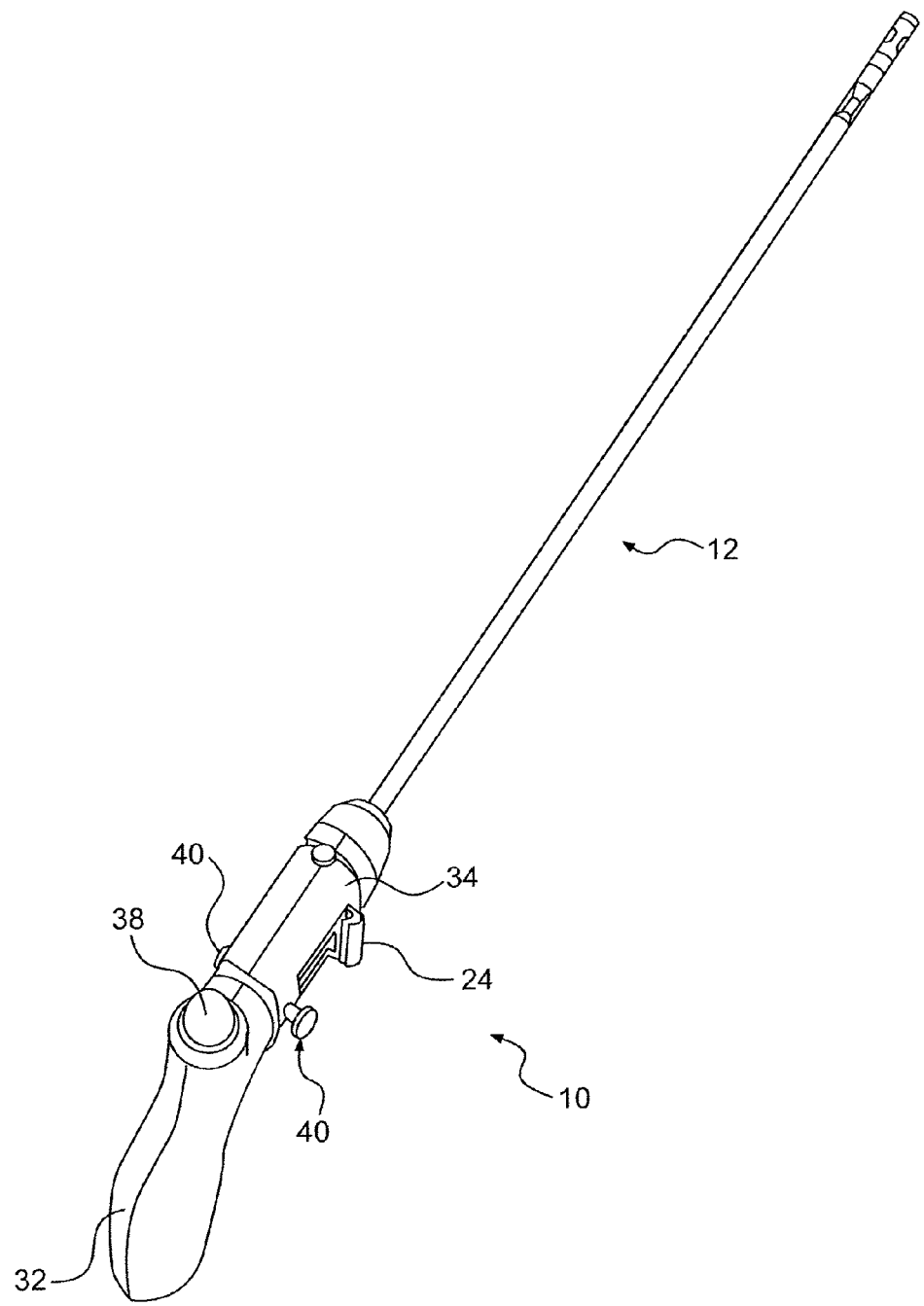
FIG. 17 shows a perspective view of the surgical instrument in an unarticulated position, according an aspect of the present disclosure.

A second embodiment of the disclosure will now be described and is shown in FIGS. 12-16 and 18. Elements which are common or equivalent among the drawings are hereinafter denoted by the same symbol, and thus a description thereof is omitted. The second embodiment is similar to the first embodiment except the proximal hinge pin knuckle 47 is replaced with a pair of coaxial proximal hinge pin pulleys 247A, 247B (referred to as proximal actuating hinge pin pulley 247A and proximal returning hinge pin pulley 247B) that are each rotatable about hinge pin 50 in opposite directions, and the distal hinge pin knuckle 54 is replaced with a pair of coaxial distal hinge pin pulleys 254A, 254B (referred to as distal actuating hinge pin pulley 254A and distal returning hinge pin pulley 254B) that are rotatable about hinge pin 58 in opposite directions. Further, link knuckles 46, 48, 52, 56 are absent in the second embodiment but may be present in alternative embodiments. As seen in FIGS. 14-16, the actuating section 44A is wound about actuating pulleys 247A, 254A such that the cable exits each pulley on the opposite pulley side the cable entered. In other words, on its way to the distal link 15 from the trigger 24, the actuating section 44A of the cable is wound about the proximal hinge pin pulley 247A and then to the distal hinge pin pulley 254A. The returning section 44B passes over returning pulleys 254B, 247B but is not wound thereabout on its way back to the trigger 24 from the distal link 15.

The actuating hinge pin pulleys 247A, 254A each may have helical channels in their outer circumferences to increase the contact area of the actuating section 44A of the cable with the pulleys; however, those of skill in the art will appreciate that in alternative embodiments there outer circumference may include other suitable configurations, such as a single channel or a flat surface over which the cable may be wound. The returning hinge pin pulleys 247B, 254B each has a single channel to guide the returning section 44B; however, those of skill in the art will appreciate that in alternative embodiments there outer circumference may include other suitable configurations, such as helical channels over which the returning section 44B may be wound, or a flat surface.

The cable or cables 44A, 44B of the second embodiment are routed as explained herein. As shown, e.g., in FIG. 14-16, from the trigger 24, the actuating section 44A passes along the inner side of the lumen 12 until it arrives at the proximal knuckle 26. Once at the proximal knuckle 26, the actuating section 44A encircles the actuating proximal hinge pin pulley 247A by approximately 360 degrees and continues to the distal knuckle 28. Once at the distal knuckle, the actuating section encircles the actuating distal hinge pin pulley 254A by approximately 360 degrees and continues into the distal articulated segment 15 where the cable is affixed (i.e., translation of the cable is prevented). In embodiments where two cables is used, the preceding is the terminus of the actuating section 44A, and a new cable in the form of the returning section 44B is returned back to the trigger 24 on the opposite side of the device. In embodiments where a single cable is used, after the actuating section 44A is affixed to the distal articulated segment 15 the returning section 44B is returned back to the trigger 24 on the opposite side of the device. Irrespective of whether single or plural cables are used, the returning section 44B is routed from the distal segment 15 to the trigger 24 as follows: On its way back to the trigger and at the distal knuckle 28, the returning section 44B passes over the returning distal hinge pin pulley 254B and continues on to the proximal knuckle 26, where the returning section 44B passes over the returning proximal hinge pin pulley 247B. After passing over the returning proximal hinge pin pulley 247B, the returning section 44B passes through the lumen 12 and into the handpiece 16 where the returning section is fastened to the trigger 24. Also irrespective of whether single or plural cables 44A, 44B are used, it is preferable to prevent the cable from translating about the distalmost portion of cable travel, otherwise the cable will not articulate the links 14, 15, but will rather rotate in place like a conveyor belt.

In embodiments where a single articulating cable 44A, 44B is used, an adjustment mechanism (also referred to as an adjuster) 60 positioned in the distal link 15 may be used to secure the cable in place, preferably at the distalmost point of travel of the cable. The adjuster 60 includes a locking bar 62 extending through the distal link 15 in a direction generally parallel with the distal hinge pin and about which the distal end of the actuation cable bends at the distal articulable segment, taking approximately a 180 degree turn, and is the point at which the actuating section 44A becomes the returning section 44B, and vice versa. It is also preferred that the adjuster is located proximal of the tip attachment section 30. The circumference of the locking bar 62 may have a helical or other channel into which the cable is positioned, to increase the contact area of the locking bar 62 with the cable 44A, 44B and to facilitate adjustment of the cable. The adjuster 60 also includes a cam bar 64 positioned distal of the locking bar such that the cable is sandwiched between the locking bar and the cam bar. The cam bar 64 extends in a direction generally parallel with the locking bar 62 and preferably has an eccentric outer circumference such that rotation of the cam bar causes the cam bar to press the cable 44A, 44B against the locking bar to prevent translation of the cable, or alternatively loosens the cam bar from pressing against the cable. In this manner the cam bar 64 may selectively apply pressure against the cable 44A, 44B, or disengage from the cable. The adjuster 60 may be used to prevent translation of the cable during initial assembly of the instrument, or may be used by the user during the instrument's life to tighten the cable should any slack develop during use. To do so, the user may insert a screwdriver or other tool into the cam bar 64 to rotate the cam bar within the distal link. It is also noted that the adjuster may be used in any of the embodiments disclosed herein.

As with the previous embodiment, the articulation of the instrument 10 is started when the user uses a finger to proximally pull the trigger 24, which in turn tenses the actuating section 44A. Tension in the actuating section 44A translates over the actuating hinge pin pulleys 247A, 254A through their helical circumferences and also causes actuating hinge pin pulleys 247A, 254A to rotate about their respective hinge pins 50, 58 (in the counterclockwise direction when viewing FIG. 16). Tension in the returning section 44B also loosens such that the returning section 44B translates over the returning pulleys 247B, 254B and also causes returning hinge pin pulleys to rotate about their respect hinge pins 50, 58 (in the clockwise direction when viewing FIG. 16, i.e., in a direction opposite to the rotation direction of the actuating hinge pin pulleys 247A, 254A). Thus, when combined with the movement of the actuating pulleys 247A, 254A in the actuating section 44A, the links 14, 15 begin to articulate, thereby deflecting the instrument 10.

While the hinge pin pulleys 247A, 247B, 254A, 254B are separate components from the hinge pins 50, 58, in alternative embodiments they may be integrated such that each pulley has an axle that rotates within a respective journal in the walls of the insertion portion.

For illustrative purposes, in FIGS. 12-13 the actuating (bending) direction of the links 14, 15 is counterclockwise; in FIGS. 14-15 the actuating direction of the links 14, 15 is into the page; in FIG. 16 the actuating direction of the links 14, 15 is clockwise; and in FIG. 18 the actuating direction of the links 14, 15 is downward.

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in its aspects. Although the invention has been described with reference to particular means, materials and embodiments, the invention is not intended to be limited to the particulars disclosed; rather the invention extends to all functionally equivalent structures, methods, and uses such as are within the scope of the appended claims.

For example, while the present disclosure has been described with reference to performing a surgical procedure via linkage between the surgeon's finger and the instrument 10, it is appreciable by those of skill in the art that the present invention may be used in non-surgical procedures, including but not limited to manufacturing and construction, and the instrument may be actuated by a machine instead of a finger.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. §1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. An instrument comprising:
    a lumen having a proximal end and a distal end;
    a handpiece affixed to the proximal end of the lumen and including an actuator;
    a proximal articulable segment having a proximal end and a distal end, the proximal end of the proximal articulable segment pivotably attached to the distal end of the lumen via a proximal hinge pin extending in a direction generally perpendicular to a longitudinal axis of the lumen;
    a distal articulable segment having a proximal end and a distal end, the proximal end of the distal articulable segment pivotably attached to the distal end of the proximal articulable segment via a distal hinge pin extending in the direction generally perpendicular to the longitudinal axis of the lumen;
    an actuation cable extending from the actuator through the lumen and into the proximal articulable segment; and
    a cable router comprising:
        a proximal pulley assembly rotatable about the proximal hinge pin, wherein the cable is wrapped about the proximal pulley assembly; and
        a distal knuckle assembly comprising a distal pulley assembly rotatable about the distal hinge pin, wherein the cable is wrapped about the distal pulley assembly, wherein:
        the proximal articulable segment is limited in travel about the proximal hinge pin to a range of approximately 0 and approximately 90 degrees of the longitudinal axis of the lumen, and
        the distal articulable segment is limited in travel about the distal hinge pin to a range of approximately 0 and approximately 90 degrees of a longitudinal axis of the proximal articulable segment such that the distal articulable segment is limited in travel to a range of approximately 0 and approximately 180 degrees of the longitudinal axis of the lumen.

2. The instrument of claim 1, wherein the cable is wrapped approximately 360 degrees about the proximal pulley assembly.

3. The instrument of claim 1, wherein during tensioning of the actuation cable to pivot the proximal articulable segment to a position oblique to the lumen, the cable translates about the proximal pulley assembly and causes the proximal pulley assembly to rotate.

4. The instrument of claim 1, wherein an outer circumference of the proximal pulley assembly has a helical channel through which the cable is wrapped.

5. The instrument of claim 1, wherein the cable is wrapped approximately 360 degrees about the distal pulley assembly.

6. The instrument of claim 1, wherein an outer circumference of the distal pulley assembly has a helical channel through which the cable is wrapped.

7. The instrument of claim 1, further comprising an adjuster affixed to a distal end of the actuation cable at the distal articulable segment, wherein:
    the actuation cable is a single cable extending from the actuator through the lumen, the proximal articulable segment, the distal articulable segment, and back to the actuator, the actuation cable comprising:
        an actuating section bent about the proximal segment knuckle, the lumen knuckle and the proximal pulley assembly and configured to pivot the proximal articulable element relative to the lumen; and
        a returning section generally parallel with the proximal articulable segment and the lumen and configured to return the proximal articulable segment generally parallel with the lumen; and
    the adjuster is configured to prevent translation of the actuation cable about the distal end of the distal articulable segment.

8. The instrument of claim 7, wherein the adjuster further comprises:

a locking bar extending in a direction generally parallel with the distal hinge pin and about which the distal end of the actuation cable bends at the distal articulable segment; and a cam bar positioned at the distal articulable element and configured to removably adjustably prevent translation of the actuation cable by removably adjustably impinging the actuation cable against the locking bar.

9. The instrument of claim 8, wherein an outer circumference of the locking bar has a helical channel through which the cable is bent.

10. The instrument of claim 7, wherein in a radial direction, an angle created by the actuating section of the actuation cable and the returning section of the actuation cable with a longitudinal axis of the lumen is oblique.

11. The instrument of claim 1, wherein a distalmost end of the distal articulable segment is configured to removably accommodate a surgical tool therein.

12. The instrument of claim 1, wherein:
the proximal pulley assembly comprises first and second proximal pulleys coaxially rotatable about the proximal hinge pin;
the actuation cable comprises:
an actuating section wrapped about the first proximal pulley; and
a returning section wrapped about the second proximal pulley; and
during actuation of the actuation cable, the actuating section translates over and causes the first proximal pulley to rotate about the proximal hinge pin, and the returning section translates over and causes the second proximal pulley to rotate about the proximal hinge pin in a direction opposite the rotation direction of the first proximal pulley.

13. The instrument of claim 1, wherein:
the proximal pulley assembly comprises first and second proximal pulleys coaxially rotatable about the proximal hinge pin;
the distal pulley assembly comprises first and second distal pulleys coaxially rotatable about the distal hinge pin;
the actuation cable comprises:
an actuating section wrapped about the first proximal pulley and first distal pulley; and
a returning section wrapped about the second proximal pulley and second distal pulley; and
during actuation of the actuation cable, the actuating section translates over and causes the first proximal and distal pulleys to respectively rotate about the proximal and distal hinge pins, and the returning section translates over and causes the second proximal and distal pulleys to respectively rotate about the proximal and distal hinge pins in a direction opposite the rotation direction of the first proximal and distal pulleys.

14. The instrument of claim 1, wherein the actuation cable comprises stainless steel wire strands.

15. The instrument of claim 1, wherein the proximal articulable segment is limited in travel about the proximal hinge pin to a range of 0 and 90 degrees of the longitudinal axis of the lumen.

16. The instrument of claim 1, wherein the handpiece comprises an articulation lock configured to removably lock the actuator such that the proximal articulable segment is correspondingly locked from pivoting.

17. The instrument of claim 1, wherein the handpiece comprises:
a nosepiece and a handle; and a handle rotation release located on one of the nosepiece and handle and configured to removably lockably provide for the rotatable positioning of the handle relative to the nosepiece.

18. The instrument of claim 1, wherein the actuation cable has a diameter of approximately 0.027 of an inch.

19. The instrument of claim 1, wherein the outer diameter of the lumen is approximately 5 millimeters.

20. A method of operating an instrument, the instrument having:
a lumen having a proximal end and a distal end;
an actuator affixed to the proximal end of the lumen;
a proximal articulable segment having a proximal end and a distal end, the proximal end of the proximal articulable segment pivotably attached to the distal end of the lumen via a proximal hinge pin extending in a direction generally perpendicular to a longitudinal axis of the lumen;
a distal articulable segment having a proximal end and a distal end, the proximal end of the distal articulable segment pivotably attached to the distal end of the proximal articulable segment via a distal hinge pin extending in the direction generally perpendicular to the longitudinal axis of the lumen;
an actuation cable extending from the actuator through the lumen and into the proximal articulable segment; and
a cable router having:
a proximal knuckle assembly having:
a proximal segment knuckle affixed to an inner wall of the proximal end of the proximal articulable segment;
a lumen knuckle affixed to an inner wall of the distal end of the lumen; and
a proximal hinge pin knuckle affixed about the proximal hinge pin at a position between the proximal segment knuckle and the lumen knuckle, wherein the cable is bent against the proximal segment knuckle, the lumen knuckle and the proximal hinge pin knuckle when the proximal articulable segment is generally parallel with the lumen; and
a distal knuckle assembly having a distal pulley assembly rotatable about the distal hinge pin, wherein the cable is wrapped about the distal pulley assembly, the method comprising:
initially actuating the actuator to provide tension the actuation cable over the proximal segment knuckle and lumen knuckle such that the actuation cable exerts a force against the proximal hinge pin knuckle in a direction generally orthogonal to the longitudinal axis of the lumen;
subsequently actuating the actuator, subsequent to said initially actuating, such that the actuation cable exerts a force in a direction different from the force against the proximal hinge pin knuckle and translates the actuation cable over the proximal segment knuckle and lumen knuckle;
articulating the proximal articulable segment relative to the lumen;
limiting travel of the proximal articulable segment about the proximal hinge pin to a range of approximately 0 and approximately 90 degrees of the longitudinal axis of the lumen; and
limiting travel of the distal articulable segment about the distal hinge pin to a range of approximately 0 and approximately 90 degrees of a longitudinal axis of the proximal articulable segment such that the distal articulable segment is limited in travel to a range of approximately 0 and approximately 180 degrees of the longitudinal axis of the lumen.

* * * * *